US00PP35391P2

(12) United States Plant Patent
Podaras

(10) Patent No.: US PP35,391 P2
(45) Date of Patent: Sep. 19, 2023

(54) ***BUDDLEIA* PLANT NAMED 'PODARASNGA 9-15'**

(50) Latin Name: ***Buddleia* x *hybrida (Buddleia davidii* x *B. crispa* x *B. alternafolia* x *B. lindleyana)***
Varietal Denomination: PODARASNGA 9-15

(71) Applicant: Early Morning LLC, Greendale, IN (US)

(72) Inventor: Peter Podaras, Boring, OR (US)

(73) Assignee: Early Morning, LLC, Greendale, IN (US)

( * ) Notice: Subject to any disclaimer, the term of this patent is extended or adjusted under 35 U.S.C. 154(b) by 0 days.

(21) Appl. No.: 17/978,414

(22) Filed: Nov. 1, 2022

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
See application file for complete search history.

(56) References Cited

PUBLICATIONS https://www.soonerplantfarm.com/plant/butterfly-bush-blueberry-pie.*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new *Buddleia* plant particularly distinguished by contrasting white eye surrounded by dark purple flowers, a small statured plant that is wider than tall, large and dense panicles and continuous blooming, is disclosed.

5 Drawing Sheets

Genus and species: *Buddleia* x *hybrida* (*Buddleia davidii* x *B. crispa* x *B. alternafolia* x *B. lindleyana*).
Variety denomination: 'PODARASNGA 9-15'.

BACKGROUND OF THE NEW PLANT

The present invention relates to a new and distinct variety of *Buddleia* hereinafter referred to by the variety name 'PODARASNGA 9-15'.

'PODARASNGA 9-15' arose from a deliberate cross between two un-named, proprietary and unpatented *Buddleia* seedlings in Salem, Oreg. Seeds from the cross were sown in April 2014 in Salem Oreg. and further grown in Tipp City, Ohio. 'PODARASNGA 9-15' was selected in July 2017 in Tipp City, Ohio from the seedling population.

'PODARASNGA 9-15' was first asexually propagated in August 2017 in Tipp City, Ohio by softwood cuttings. 'PODARASNGA 9-15' was found to reproduce true to type in successive generations of asexual propagation via softwood cuttings.

SUMMARY

The following are the most outstanding and distinguishing characteristics of this new variety when grown under normal horticultural practices in Boring, Oreg. and Tipp City, Ohio.

1. Contrasting white eye surrounded by dark purple flowers;
2. Small statured plant that is wider than tall;

3. Large and dense panicles; and
4. Continuous blooming.

DESCRIPTION OF THE PHOTOGRAPHS

This new *Buddleia* plant is illustrated by the accompanying photographs which shows the plant's overall plant habit including form, inflorescence, and foliage. The photographs are of a 5-month-old plant taken in September 2022 and grown outdoors in Boring, Oreg. The colors shown are as true as can be reasonably obtained by conventional photographic procedures.

DESCRIPTION OF THE NEW VARIETY

Figure 1:
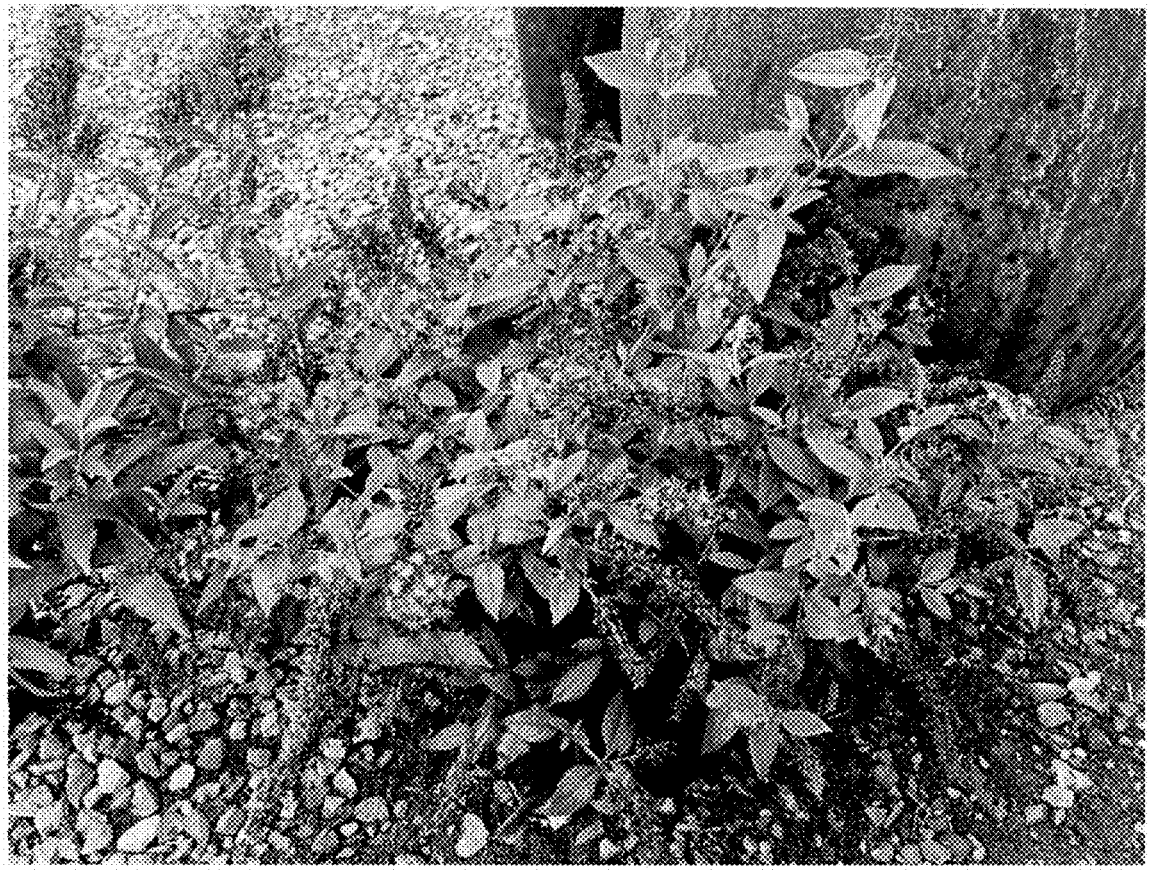
FIG. 1 shows the overall plant habit.
Figure 2:
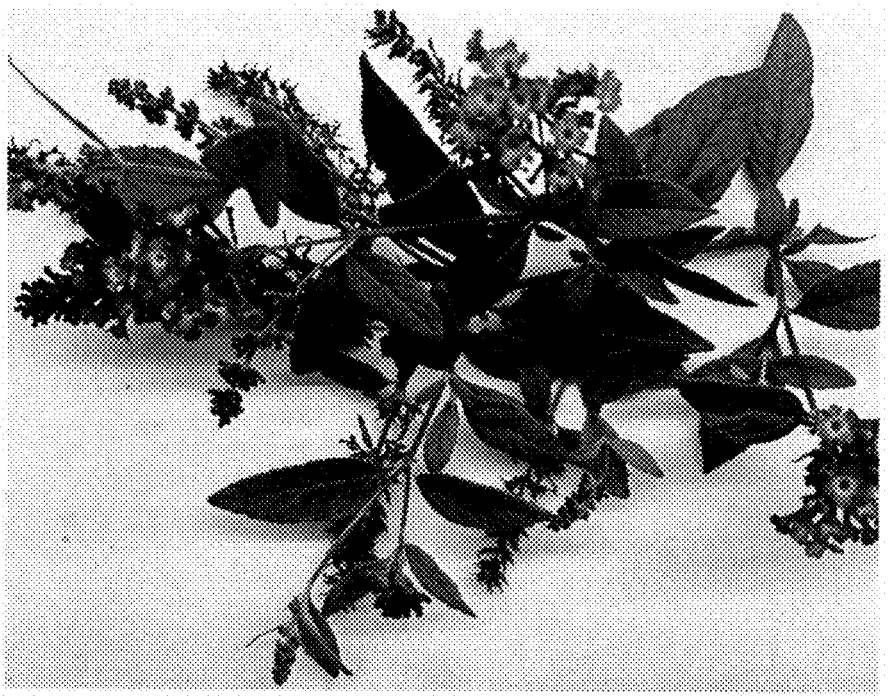
FIG. 2 shows the upper surface of multiple flowering stems of 'PODARASNGA 9-15' at different stages of flowering.
Figure 3:
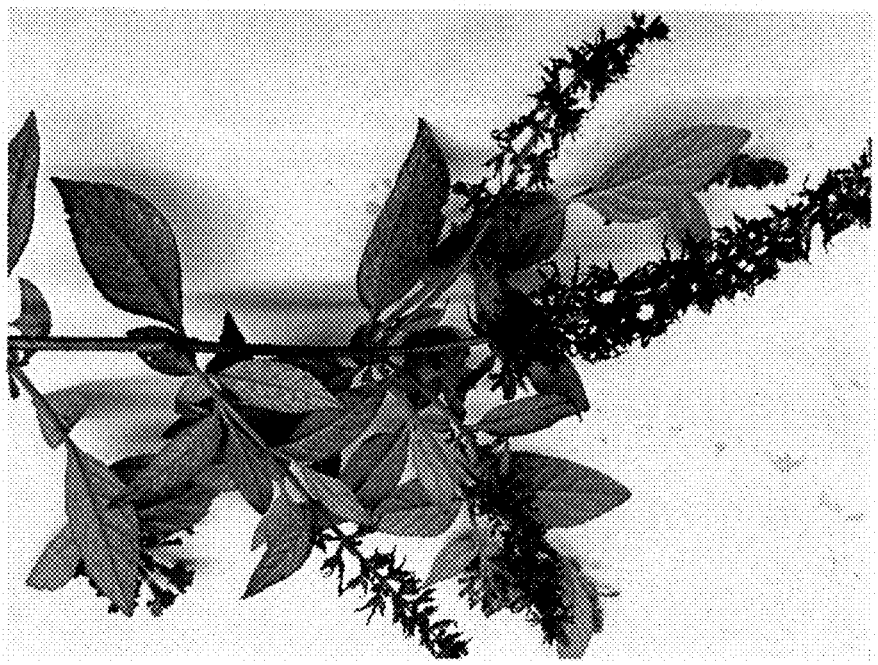
FIG. 3 shows the lower surface of FIG. 2.
Figure 4:
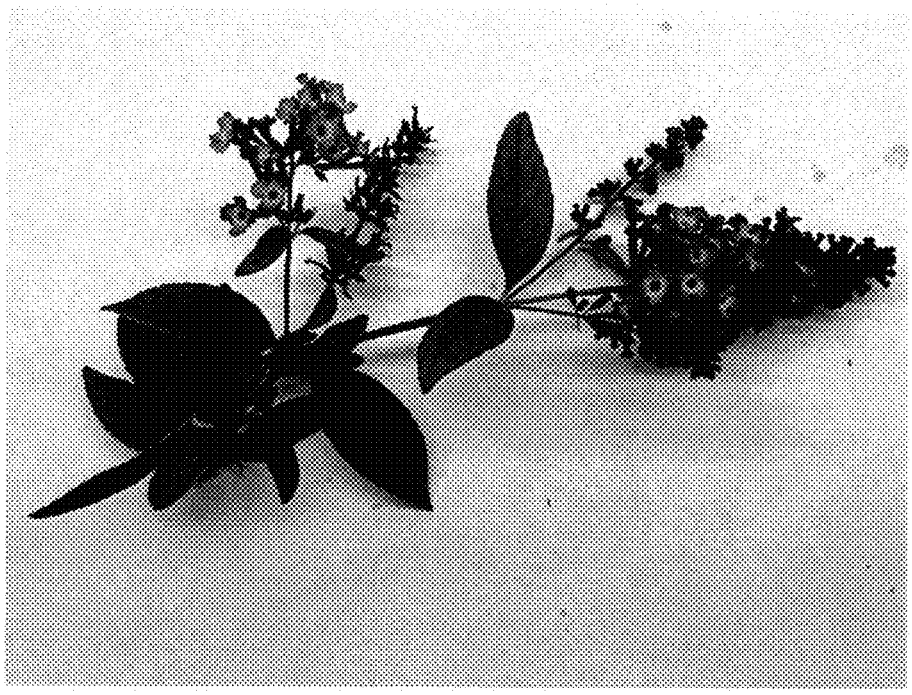
FIG. 4 shows the upper surface of another multiple flowering stem of 'PODARASNGA 9-15' at different stages of flowering.
Figure 5:
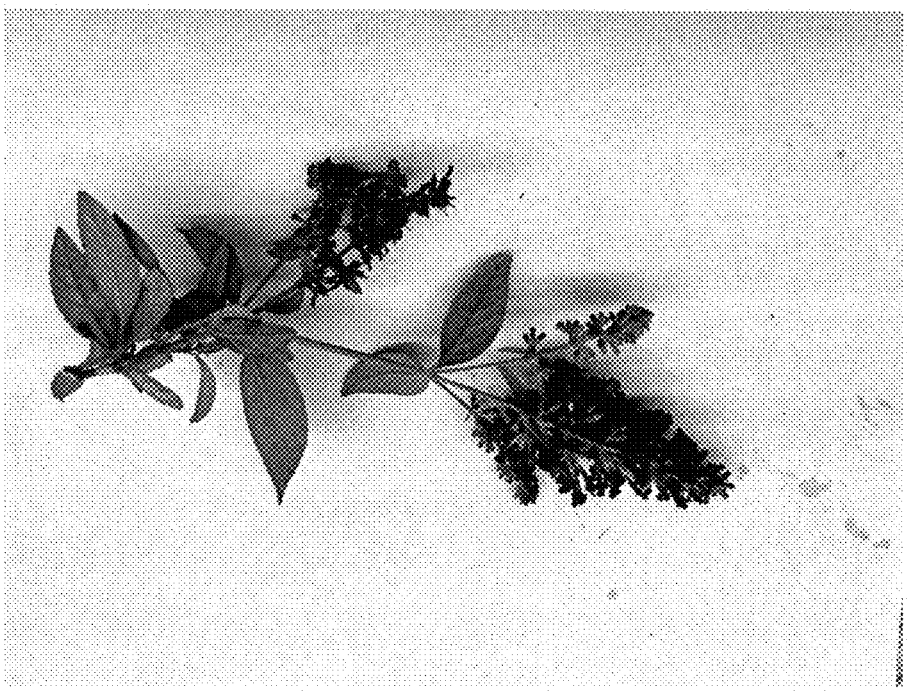
FIG. 5 shows the lower surface of FIG. 4.
Figure 6:
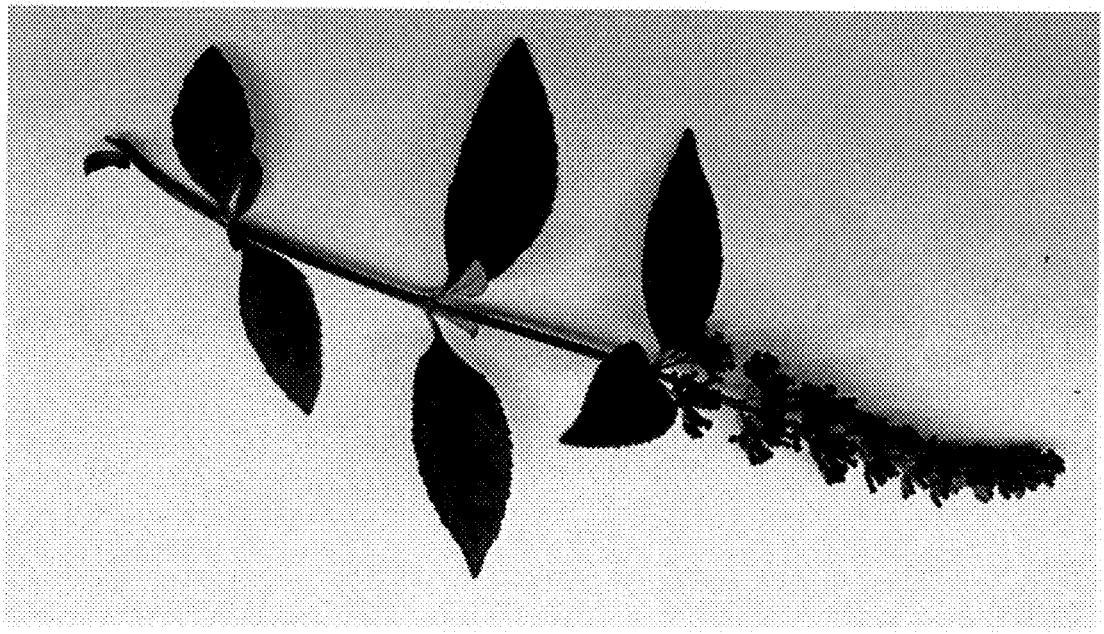
FIG. 6 shows the upper surface of an individual flowering stem of 'PODARASNGA 9-15' at bud stage.
Figure 7:
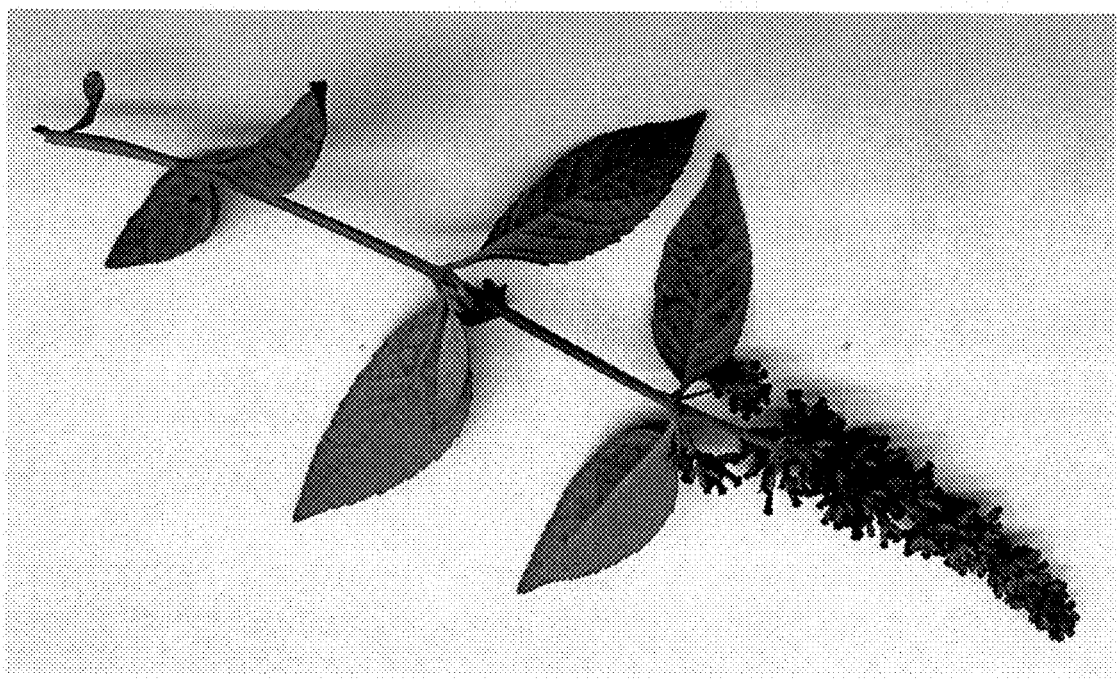
FIG. 7 shows the lower surface of FIG. 6.
Figure 8:
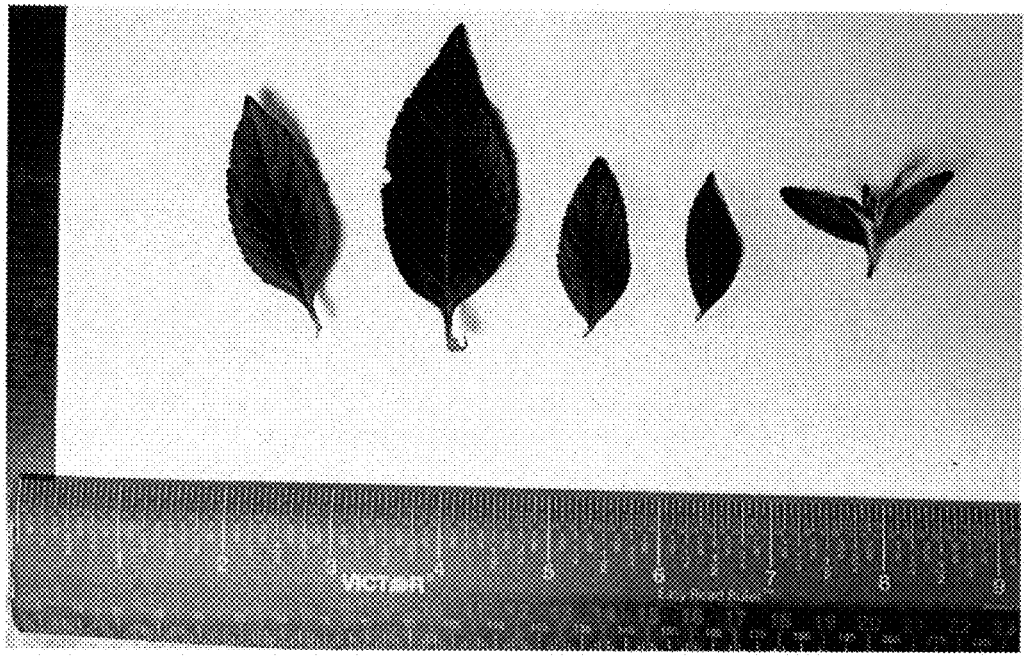
FIG. 8 shows the upper surface of individual leaves of 'PODARASNGA 9-15'.
Figure 9:
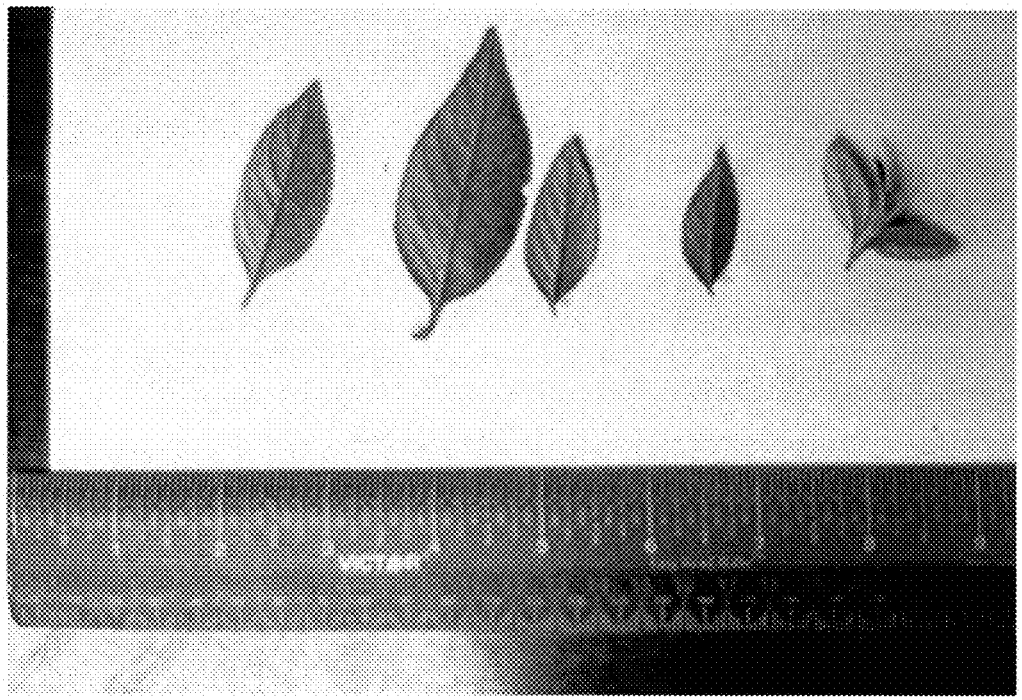
FIG. 9 shows the lower surface of the leaves of FIG. 8.

The following detailed descriptions set for the distinctive characteristics of 'PODARASNGA 9-15'. Measurements were taken from a 5-month-old plant, potted in a 3-gallon container and grown outdoors under irrigation. Color references are to The R.H.S. Colour Chart of The Royal Horticultural Society of London (R.H.S.) 2001, Fourth Edition.

Classification:

*Family*.—Scrophulariacace.

*Botanical*.—*Buddleia* x *hybrida* (*Buddleia davidii* x *B. crispa* x *B. alternifolia* x *B. lindleyana*).

*Designation*.—'PODARASNGA 9-15'.

Plant:

*Type and habit*.—Deciduous shrub with a compact and mounding growth habit; has a profuse number of flowers at each branch terminus; readily produces branches at each node; has horizontal branches with vertical secondary branches terminating in an inflorescence.

*Form*.—Oval, horizontal and low to the ground.

*Height* (*at crown and measured from the top of the soil*).—30.0 cm.

*Width* (*horizontal plant diameter*).—130 cm.

*Time to produce a finished plant*.—To produce a 4-inch plant: 5 to 6 weeks from cuttings. To produce a 1-gallon pot: 8 to 10 weeks.

*Outdoor plant performance*.—Excellent in average soil structure with full sun; average fertility and water usage.

*Natural flowering season*.—At least 4 weeks before *B. davidii* and continuing up to a hard frost.

*Time to initiate and develop roots*.—7 to 10 days using 3,000 to 4,000 ppm IBA (indolebutyric acid) for tougher plant material or 2,000 ppm IBA for softer plant material.

*Root description and habit*.—Dense and fibrous; roots are RHS 18D.

*Propagation type*.—Softwood cuttings.

*Hardiness*.—Hardy to USDA Zone 6, possibly hardy in USDA Zone 5b; pruning is not recommended after August.

Lateral branches:

*General*.—Young branches are cubic and are 4-sided, while mature branches are rounded.

*Quantity per plant*.—About 10 primary branches.

*Length*.—41.0 cm to 52.0 cm for primary branches and 12 cm to 22 cm for secondary branches.

*Internode length*.—About 0.4 cm.

*Diameter, for all branches*.—About 0.5 cm; from midpoint, about 0.25 cm.

*Color*.—Inner and older branches not exposed to the sun form a splotchy bard of RHS 199A and RHS N200A; outer younger branches exposed to sun are RHS N186A and inner younger branches not exposed to the sun are RHS 191A.

*Angle of branch attachment*.—About 180 degrees for primary branches and about 90 degrees for secondary branches which are pliable.

*Texture*.—Primary branches are rough due to a developing thin bark and secondary branches are soft due to being floccose.

*Strength*.—Mature branches are pliable.

*Anthocyanin*.—RHS N186A.

Leaves:

*Leaf arrangement and quantity*.—135 to 200 per branch; opposite; about 5 pairs of leaves on the primary branches; about 4 pairs of leaves on the secondary and tertiary branches.

*Length*.—2.5 nearest to flower panicles and 8 cm at base of plant.

*Width*.—1 cm to 3 cm.

*Shape*.—Ovate.

*Apex*.—Apiculate.

*Base*.—Shortly attenuate.

*Margin*.—Broadly serrate and each point of the margin comes to a rounded point.

*Texture*.—Upper surface: Rugose with stellate hairs; glandular RHS N155A bodies are present. Lower surface: Thickly floccose; glandular RHS N155A bodies are found under the hairs.

*Color, immature*.—Upper surface: RHS 137A. Lower surface: RHS 195A.

*Color, mature*.—Upper surface: RHS 137A. Lower surface: RHS 194A.

*Venation pattern*.—Pinnate with RHS 155A papillate glands on the veins.

*Venation color*.—Upper surface: RHS 196C. Lower surface: RHS 194A.

*Petiole*.—Length: 0.9 cm. Diameter: 0.19 cm. Texture: Strongly floccose. Color: RHS 196C.

Inflorescence (panicle):

*Appearance*.—Panicles are lanceolate-conical to oval-conical in shape; terminal flowers are in fours, with an additional flower at the left-side node; additionally, a fifth or sixth flower may be found.

*Height*.—Of primary inflorescence/panicle: Between about 12.5 cm to 15.0 cm. Of three axillary inflorescence/panicles: Between about 7.0 cm to 9 cm. Of one axillary inflorescence/panicle: 1.5 cm to 6.0 cm.

*Width* (*of all panicles*).—2.0 cm when the flowers are not fully open to about 3.0 cm when the flowers are fully open.

*Bud*.—General: Buds begin as a bud cluster and are RHS 145A with RHS N92A at the tip and as the buds mature, they become individualized and enlarge; the length of the bud cluster is 1.0 cm and the width of the bud cluster is 0.4 cm. Shape: Strongly conical. Texture: Floccose. Length: 2.0 cm. Width: 0.5 cm. Color: Mainly RHS 141B with RHS N92A.

*Flower*.—Type and habit: Single and salverform flowers arranged in compound terminal panicles which are conical in shape; flowers face upright and outward. Fragrance: Very fragrant. Lastingness of flowers on the plant: 7 to 10 days. Quantity of flowers per inflorescence (panicle): About 1006. Depth: 2.0 cm. Diameter: 1.0 cm.

*Petals*.—Arrangement: Four, sometimes five or six, partially cupped petals arranged in a single whorl with the petals fused to form a tube. Shape: Square. Apex: Partially cupped. Base: Fused. Margin: Crenulate. Texture (both upper and lower surfaces): Very few hairs and small RHS N115A glandular bodies sprinkled on petals. Length: 0.4 cm. Width: 0.4 cm. Color, immature (both upper and lower surfaces): RHS N92B. Color, mature: Upper surface: RHS N89B. Lower surface: RHS 83A.

*Eye color*.—RHS 155B: between the petals and top of the corolla tube.

*Corolla tube*.—Length: 0.9 cm. Width: 0.1 cm. Color: Inner surface: RHS 163B. Outer surface: RHS 83A mainly to RHS 77A with RHS 14B near the sepal. Texture: Inner surface: Smooth except for spines present that are 0.015 cm in length. Outer surface: Papillate with white glandular bodies and a few hairs.

*Calyx*.—Arrangement and quantity per flower: Four sepals arranged in a single whorl and fused at the base. Sepals: Shape: Cup-shaped. Apex: Lobed. Base: Fused. Margin: Entire. Length: 0.3 cm. Width: 0.1 cm. Texture: Upper surface: Floccose with white glandular bodies. Lower surface: Smooth. Color: Upper surface: RHS N92B. Lower surface: 141B.

*Peduncle*.—Shape: Square. Length: 2.0 cm to 4.0 cm. Diameter: 0.2 cm. Strength: Flexible and strong. Color: RHS N186A exposed to the sun and RHS 191A when not exposed to the sun. Texture: Floccose.

*Pedicel*.—Length: 0.3 cm. Diameter: 0.1 cm. Color: RHS 141B. Texture: Floccose.

Reproductive organs:

*Stamens*.—Quantity per flower: 4. Filament: General: Completely fused to corolla tube. Anther: Length: 1.0 cm. Color: RHS 155C. Pollen amount: Moderate. Pollen color: RHS 155C.

*Pistil*.—Quantity per flower: 1. Length: 0.4 cm. Stigma: Shape: Club shaped with obtuse tip, so narrow at the base and wide at the tip with a barely noticeable cleft. Color: RHS 144B. Style: Length: 0.1 cm. Color: RHS N194A. Ovary: Shape and position: Globular and superior. Width: 0.09 cm. Length: 0.2 cm. Color: RHS 144B with.

Seed: Seed not observed to date.

Disease and insect resistance: None specific disease or insect resistant observed.

COMPARISON WITH COMMERCIAL VARIETY

When 'PODARASNGA 9-15' is compared to the commercial variety 'Violet Cascade' (U.S. Plant Pat. No. 34,298), 'PODARASNGA 9-15' is 30.0 cm in height, while 'Violet Cascade' is 122 cm in height.

When 'PODARASNGA 9-15' is compared to the female parent, an un-named, unpatented proprietary *Buddleia* hybrid, 'PODARASNGA 9-15' is shorter in height than the female parent and broader in width than the female parent with much more contrasting white eye than the female parent.

When 'PODARASNGA 9-15' is compared to the male parent, an un-named, unpatented proprietary *Buddleia* hybrid, 'PODARASNGA 9-15' is shorter and broader with darker coloration in the outer portion of the petal than the male parent.

I claim:

1. A new and distinct cultivar of *Buddleia* plant named 'PodarasNGA 9-15' as described and illustrated herein.

* * * * *